United States Patent [19]

Gastinger et al.

[11] Patent Number: 4,769,508

[45] Date of Patent: * Sep. 6, 1988

[54] ALKALI PROMOTED MANGANESE OXIDE COMPOSITIONS CONTAINING TITANIUM

[75] Inventors: Robert G. Gastinger, Brookhaven; Howard P. Withers, Jr., Douglassville; John A. Sofranko, Malvern, all of Pa.

[73] Assignee: Atlantic Richfield Company, Los Angeles, Calif.

[*] Notice: The portion of the term of this patent subsequent to Feb. 12, 2002 has been disclaimed.

[21] Appl. No.: 864,644

[22] Filed: May 15, 1986

Related U.S. Application Data

[62] Division of Ser. No. 683,123, Dec. 18, 1984, abandoned.

[51] Int. Cl.$^4$ .................................................. C07C 2/00
[52] U.S. Cl. .................................... 585/500; 585/654; 585/656; 585/661; 585/700; 585/943
[58] Field of Search ............... 585/654, 656, 658, 661, 585/500, 700, 943

[56] References Cited

U.S. PATENT DOCUMENTS

| | | | |
|---|---|---|---|
| 2,148,140 | 2/1939 | Tripsch | 585/654 |
| 2,608,534 | 8/1952 | Fleck | 585/654 |
| 4,239,658 | 12/1980 | Mitchell, III et al. | 585/500 |
| 4,310,717 | 1/1982 | Eastman et al. | 585/661 |
| 4,450,313 | 5/1984 | Eastman et al. | 585/661 |
| 4,495,374 | 1/1985 | Jones et al. | 585/943 |
| 4,497,971 | 2/1985 | Eastman et al. | 585/661 |
| 4,499,322 | 2/1985 | Jones et al. | 585/943 |
| 4,523,049 | 6/1985 | Jones et al. | 585/943 |
| 4,547,611 | 10/1985 | Jones et al. | 585/943 |

*Primary Examiner*—William R. Dixon, Jr.
*Assistant Examiner*—James M. Hunter, Jr.
*Attorney, Agent, or Firm*—Craig E. Larson

[57] ABSTRACT

A class of mixed oxide catalysts comprising Mn-containing oxides, alkali metals or compounds thereof, and at least one member of the group consisting of oxides of Ti, mixed oxides of Ti and Si, and mixed oxides of Ti and at least one alkaline earth metal. In the more preferred embodiments, the third component serves as a carrier for the Mn and alkali metal components. The composition preferably comprises a major amount of the carrier material and minor amounts of the other components. The compositions are useful for hydrocarbon conversion, methane conversion, and oxidative dehydrogenation processes characterized by formation of coproduct water.

3 Claims, No Drawings

ALKALI PROMOTED MANGANESE OXIDE COMPOSITIONS CONTAINING TITANIUM

This is a division of application Ser. No. 683,123, abandoned, filed Dec. 18, 1984.

BACKGROUND OF THE INVENTION

The present invention relates to compositions comprising oxides of Mn and and alkali metals. More specifically, the present invention relates to compositions comprising oxides of Mn, alkali metals, and a third component containing oxides or mixed oxides of Ti. The present invention also relates to hydrocarbon conversion processes employing alkali metal promotoed Mn oxide compositions. In one particular aspect, it relates to methods for converting methane to higher hydrocarbons. In another particular aspect, it relates to processes for the oxidative dehydrogenation of hydrocarbons, especially to processes for the oxidative dehydrogenation of paraffinic hydrocarbons to the corresponding mono-olefins. The central aspect of the presently claimed invention is the catalyst composition employed in such hydrocarbon conversion processes.

Hydrocarbon conversion processes employing the composition of this invention are characterized by relatively severe reaction conditions and by the formation of coproduct water. Thus, hydrothermal stability at elevated temperature (e.g., 500° to 1000° C.) is an important criteria for the compositions. Moreover, uses contemplated for the present compositions require catalysts which are rugged, attrition-resistant, and stable at high temperatures. It is also desirable that the compositions are able to operate effectively for relatively long periods while cycling between oxidized and reduced states.

An object of the present invention is a composition and process for hydrocarbon conversion processes, especially for processes characterized by the formation of byproduct water. A related object is a rugged, stable, attrition-resistant oxidant composition for such processes.

Another object of the present invention is a composition and process for converting methane to higher hydrocarbons, especially for processes characterized by the formation of byproduct water. A related object is a rugged, stable, attrition-resistant oxidant composition for such methane conversion processes.

Still another object of the present invention is a composition and process for the oxidative dehydrogenation of hydrocarbons. A related object is a rugged, stable, attrition-resistant oxidant composition for such processes. Another related object is a composition and process for the oxidative dehydrogenation of paraffinic hydrocarbons to form the corresponding mono-olefins.

Other objects, aspects and advantages of the invention will be apparent to those skilled in the art upon studying the specification and the appended claims.

SUMMARY OF THE INVENTION

This invention is a class of catalyst compositions comprising:
(a) Mn-containing oxides,
(b) at least one alkali metal or compound thereof, and
(c) at least one member of the group consisting of oxides of Ti, mixed oxides of Ti and Si, and mixed oxides of Ti and at least one alkaline earth metal. The compositions are characterized by Mn content and by the ratio of alkali metal: Mn. In general, preferred compositions contain more than about 50 wt. % of component (c), more preferably they contain more than about 60 wt. % of component (c). Stated in another way, Mn is preferably present in an amount within the range of about 1 to 40 wt. % based on the combined weight of Mn and component (c). The atomic ratio of alkali metal: Mn is preferably within the range of about 0.01 to 10:1.

Alkali metals are selected from the group consisting of lithium, sodium, potassium, rubidium and cesium. Lithium, sodium and potassium, and especially lithium and sodium, are preferred alkali metals. Sodium is particularly preferred. When components (b) of the composition is sodium (or compounds thereof), the atomic ratio of Na:Mn is preferably within the range of about 0.1–3.3:1.

Alkaline earth metals are selected from the group consisting of magnesium, calcium, strontium and barium. Presently preferred members of this group are magnesium and calcium. Compositions derived from magnesia have been found to be particularly effective catalytic materials.

The compositions of this invention are useful in a variety of hydrocarbon conversion processes. When the active form of the composition (i.e., the composition in an oxidized state) is contacted with methane at elevated temperatures (e.g., at temperatures within the range of about 500° to 1000° C.), methane is converted to higher hydrocarbon products. The compositions are also effective contact agents (i.e., catalysts) in oxidative dehydrogenation processes.

DETAILED DESCRIPTION OF THE INVENTION

While the composition of the present invention is referred to as a "catalyst", it will be understood that, under conditions of use, it serves as a selective oxidant, and, therefore, takes on the characteristics of a reactant during use.

In the following formulae describing the compositions of this invention, the relative number of oxygens is designated by "x". This x is variable because the compositions may continually gain and lose oxygen during use. Thus setting a strict range of values for x would be imprecise and possibly misleading. Generally, the value ascribed to x falls within the range of the number of oxygens required in the higher oxidation states (the "active" or "oxidized" composition) to the number of oxygens required in the lower oxidation states (the "reduced" composition).

The principal component of the compositions is described as "Mn-containing oxides". This term is meant to embrace both reducible oxides of Mn and reduced oxides of Mn, it being understood that reducible oxides comprise the principal active component of the composition. In its active state, then, the present composition comprises at least one reducible oxide of Mn, which oxide when contacted with methane (or higher hydrocarbons) at synthesizing (or dehydrogenation) conditions (e.g., at a temperature within the range of aboug 500° to 1000° C.) produces higher hydrocarbon products (or in the case of higher hydrocarbon dehydrogenation, dehydrogenated hydrocarbon products), coproduct water, and a reduced Mn oxide. The term "reducible" is used to identify those oxides of Mn which are reduced under the aforesaid conditions. The term "reducible oxides of Mn" includes: (1) compounds described by the general formula $Mn_xO_y$ wherein x and y designate the relative atomic proportions of metal and oxygen in the composition and/or (2) one or more oxygen-containing Mn compounds (i.e., compounds containing elements in addition to Mn and O), provided that such oxides and compounds have the capability of producing higher hydrocarbon products from methane, or of producing dehydrogenated hydrocarbons from dehydrogenatable hydrocarbons, as described herein.

In addition to Mn, other reducible metal oxides may be includes in the compositions of this invention. Examples are reducible oxides of Sn, In, Ge, Sb, Pb, Bi, Pr, Tb, Ce, Fe and Ru. However, in certain embodiments of this invention, the compositions are characterized by the substantial absence of catalytically effective Fe, to distinguish known oxidative dehydrogenation catalysts based on use of Mn ferrites.

One class of preferred compositions is characterized by the substantial absence of catalytically effective Ni and the noble metals (e.g., Rh, Pd, Ag, Os, Ir, Pt and Au) and compounds thereof, to minimize the deleterious catalytic effects of such metals and compounds thereof. For example, at the conditions (e.g., temperatures) under which the present compositions are used, these metals tend to promote coke formation and oxides of these metals tend to promote formation of combustion products ($CO_x$) rather than the desired hydrocarbons. The term "catalytically effective" is used to identify that quantity of one or more of nickel and the noble metals and compounds thereof which, when present, substantially changes the distribution of products obtained when employing the compositions of this invention.

Other additives may also be incorporated into the composition of this invention. For example, addition of a phosphorus component has been found to enhance the stability of the composition. When used, P may be present up to an amount providing a P/Mn ratio of about 2/1. If P is employed, it is desirable to provide it during catalyst preparation in the form of phosphates of alkali metals (e.g., orthophosphates, metaphosphates and pyrophosphates). Pyrophosphates are preferred. Sodium pyrophosphate is particularly preferred. P can be provided in other forms though. Examples include orthophosphoric acid, ammonium phosphates and ammonium hydrogenphosphates.

Further examples of other components which may be present in the compositions of this invention are halogen and chalcogen components. Such components may be added either during preparation of the catalysts or during use. Methane conversion processes employing halogen-promoted, reducible metal oxides are disclosed in U.S. patent application Ser. No. 600,668, filed Apr. 16, 1984, the entire content of which is incorporated herein by reference. Methane conversion processes employing chalcogen-promoted, reducible metal oxides are disclosed in U.S. patent application Ser. No. 600,659, filed Apr. 16, 1984, the entire content of which is incorporated herein by reference.

CATALYST COMPOSITIONS

One broad class of compositions within the scope of this invention comprises:

(a) Mn-containing oxides, (b) at least one alkali metal or compounds thereof, and (c) at least one member of the group consisting of oxides of Ti, mixed oxides of Ti and Si, and mixed oxides of Ti and at least one alkaline earth metal.

The amount of Mn present is preferably within the range of about 1 to 40 wt. % based on the combined weight of Mn and component (c), more preferably within the range of about 5 to 30 wt. %, the composition being substantially free of catalytically effective iron. Examples of specific embodiments within this broad class are described below.

$MnA_aTi_bO_x$

Another class of compositions within the scope of this invention comprises Mn-containing oxides, at least one alkali metal or compound thereof, and at least one oxide of Ti, said composition satisfying the formula:

$$MnA_aTi_bO_x$$

wherein A is at least one alkali metal and wherein a is within the range of about 0.01 to 10, b is within the range of about 1.5 to 70, and x is the number of oxygen atoms required by the valence of the other elements. The compositions is preferably substantially free of catalytically effective iron. Preferably, b is within the range of about 1.6 to 13. The titanium component may be provided as titania or as titanates of various metals.

$MnA_aTi_bSi_cO_x$

Another class of compositions within the scope of this invention comprises Mn-containing oxides, at least one alkali metal or compound thereof, and mixed oxides of Ti and Si, said composition satisfying the formula:

$$MnA_aTi_bSi_cO_x$$

wherein A is at least one alkali metal and wherein a is within the range of about 0.01 to 10, b is within the range of about 0.3 to 70, c is within the range of about 0.4 to 45, the ratio of b:c is within the range of about 0.01–100:1, the sum of b+c is greater than about 1, and x is the number of oxygen atoms required by the valence states of the other elements. The subscript b is preferably within the range of about 1.6 to 70, more preferably about 1.6 to 13. The subscript c is preferably within the range of about 2 to 17.

The composition may be prepared from titania and silica. However, other sources of mixed oxides may also be employed. One source of particular interest is $TiSiO_4$.

$MnA_aB_bTi_cO_x$

Another class of compositions within the scope of this invention comprises Mn-containing oxides, at least one alkali metal or compound thereof, and mixed oxides of Ti and at least one alkaline earth metal, said composition satisfying the formula:

$$MnA_aB_bTi_cO_x$$

wherein A is at least one alkali metal, B is at least one alkaline earth metal, and wherein a is within the range of about 0.01 to 10, b is within the range of about 0.1 to 90, c is within the range of about 0.3 to 70, the ratio of b: c is within the range of about 0.01 to 100:1, the sum of b+c is greater than about 1, and x is the number of oxygen atoms required by the valence states of the other elements. When B is Mg, b is preferably within the range of about 0.6 to 10. When B is Ca, b is preferably within the range of about 0.4 to 10. When B is Ba, b is preferably within the range of about 0.1 to 5.

The composition may be prepared from titania and alkaline earth oxides such as MgO, CaO, SrO and BaO. However, other sources of mixed oxides may also be employed. One source of particular interest is the alkaline earth titanates. Examples are $CaTiO_3$ (perovskite), $MgTiO_3$, $SrTiO_3$ and $Mg_2TiO_4$. One class of useful titanates is described by the general formula $Ba_xTi_yO_{x+2y}$ (e.g., $BaTiO_3$, $Ba_2TiO_4$, $Ba_4Ti_{13}O_{30}$, $Ba_6Ti_{17}O_{40}$, etc.).

CATALYST PREPARATION

The catalysts of this invention are conveniently prepared by any of the methods associated with similar compositions known in the art. Thus, methods such as precipitation, co-precipitation, impregnation, granulation, spray drying, or dry-mixing can be used. The Mn and alkali metal components can be composited or associated with the third component of the composition by any of the methods associated with the preparation of supported catalyst compositions known in the art. Such "supported" compositions may be prepared by methods such as adsorption, impregnation, precipitation, co-precipitation, granulation, spray drying, or dry mixing. Substantially any compound of the recited components can be employed in the preparation of the composition.

One suitable method of preparation is to impregnate compounds of the third component of the composition with solutions of compounds of Mn and/or alkali metals. Suitable compounds for impregnation include the acetates, acetyle acetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is calcined, preferably in air at a temperature selected within the range of about 300° to 1200° C. Particular calcination temperatures will vary depending on the compounds employed.

Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred.

When the third component of the composition is mixed oxides of two of more elements, a suitable method of preparation is to prepare aqueous slurries of the oxides, add solutions containing other catalyst components and dry and calcine the resulting mixtures. Alternatively, as discussed in the above composition descriptions, the mixed oxides may be provided as preformed compounds, with the other components added as described above.

Regardless of how the components are combined, the resulting composite will generally be dried and calcined at elevated temperatures prior to use.

HYDROCARBON CONVERSION PROCESS

The catalyst compositions of the present invention are generally useful for hydrocarbon conversion processes. Contacting a hydrocarbon feed with the active composition produces hydrocarbon product, coproduct water, and a reduced catalyst composotion. The reduced catalyst composition is readily reoxidized to an active state by contact with an oxidant such as air or other oxygencontaining gases. The process may be effected in a cyclic manner wherein the catalyst is contacted alternately with a hydrocarbon feed and then with an oxygen-containing gas. The process may also be effected in a noncyclic manner wherein the catalyst is contacted concurrently with a hydrocarbon feed and an oxygen-containing gas. Operating conditions are not critical to the use of this invention, although temperatures are generally within the range of about 500° to 1000° C. Gas/solid contacting steps may be performed according to any of the known techniques: e.g., the solids may be maintained as fixed beds, fluidized beds, moving beds, ebullating beds, etc. Solids may be maintained in one contact zone or may recirculate between multiple contact zones (e.g., between oxygen-contact and hydrocarbon-contact zones).

METHANE CONVERSION PROCESS

One more specific application for the compositions of this invention is the conversion of methane to higher hydrocarbon products. The process comprises contacting a gas comprising methane with a composition comprising a reducible oxide of Mn to produce higher hydrocarbon products, coproduct water, and a composition comprising a reduced oxide of Mn. In addition to methane, the feedstock may contain other hydrocarbon or non-hydrocarbon components, although the methane content should typically be within the range of about 40 to 100 volume percent, preferably about 80 to 100 volume percent, more preferably about 90 to 100 volume percent. Operating temperatures are generally within the range of about 500° to 1000° C. Although not narrowly critical in the context of this invention, both total pressure and methane partial pressures effect results. Preferred operating pressures are within the range of about 1 to 100 atmospheres, more preferably about 1 to 30 atmospheres.

As indicated in the description of hydrocarbon conversion processes, a variety of process embodiments, including various gas/solids-contacting modes, may be employed.

OXIDATIVE DEHYDROGENATION PROCESS

Another more specific application for the composition of this invention is the dehydrogenation of dehydrogenatable hydrocarbons. The process comprises containg a gas comprising a dehydrogenatable hydrocarbon with a composition comprising a reducible oxide of Mn to produce dehydrogenated hydrocarbon products, coproduct water, and a composition comprising a reduced oxide of Mn. Dehydrogenatable hydrocarbons include a wide variety of hydrocarbons: e.g., $C_2+$ alkanes, cycloalkanes, olefines, alkylaromatics, etc. The dehydrogenated product depends in part on the feedstock selected. For example, alkanes may be dehydrogenated to form olefins, diolefins, alkynes, etc., and olefins may be dehydrogenated to form diolefins, alkynes, etc. One preferred class of feedstock comprises $C_2$–$C_5$ alkanes. One preferred process embodiment comprises oxidative dehydrogenation of $C_2$–$C_5$ alkanes to form the corresponding mono-olefins.

Operating temperatures are generally within the range of about 500° to 1000° C. Operating pressures are not narrowly critical. In general, the process is conducted within the parameters of the oxidative dehydrogenation art, but uses a novel catalyst.

What is claimed:

1. A method for converting methane to higher hydrocarbon products which comprises contacting at a temperature within the range of about 500° to 1000° C. a gas comprising methane with a solid comprising:
   (a) a reducible oxide of Mn,
   (b) at least one alkali metal or compound thereof, and
   (c) at least one member of the group consisting of oxides of Ti, mixed oxides of Ti and Si, mixed oxides of Ti and at least one alkaline earth metal.

2. The method of claim 1 wherein the amount of Mn present in said solid is about 1 to about 40 wt. %, based on the combined weight of Mn and component (c).

3. The method of claim 1 wherein the atomic ratio of alkali metal:Mn in said solid is within the range of about 0.01 to 10:1.

* * * * *